(12) United States Patent
Yamamura et al.

(10) Patent No.: US 12,405,678 B2
(45) Date of Patent: Sep. 2, 2025

(54) INPUT DEVICE AND BIOMETRIC INFORMATION DETECTION DEVICE

(71) Applicant: SEIKO EPSON CORPORATION, Tokyo (JP)

(72) Inventors: Yoshihiro Yamamura, Azumino (JP); Hidetoshi Yamamoto, Suwa (JP); Hideo Sasahara, Suwa (JP); Yuya Ozawa, Azumino (JP)

(73) Assignee: SEIKO EPSON CORPORATION, Tokyo (JP)

( * ) Notice: Subject to any disclaimer, the term of this patent is extended or adjusted under 35 U.S.C. 154(b) by 0 days.

(21) Appl. No.: 18/603,235

(22) Filed: Mar. 13, 2024

(65) Prior Publication Data

US 2024/0310930 A1    Sep. 19, 2024

(30) Foreign Application Priority Data

Mar. 14, 2023    (JP) ................. 2023-039390

(51) Int. Cl.
     *G06F 3/0354*     (2013.01)
     *A61B 5/00*     (2006.01)
     *A61B 5/024*     (2006.01)

(52) U.S. Cl.
     CPC ...... *G06F 3/03543* (2013.01); *A61B 5/02427* (2013.01); *A61B 5/6897* (2013.01)

(58) Field of Classification Search
     CPC ...... G06F 3/033; G06F 3/0386; G06F 3/0383; G06F 2203/04807; G06F 3/03543; G06F 3/03545; G06F 3/03541; G06F 3/04883; G06F 3/03542; G06F 3/03549; G06F 3/0312; G06F 21/32; G06F 3/042; G06V 40/1341

See application file for complete search history.

(56) References Cited

U.S. PATENT DOCUMENTS

| | | | |
|---|---|---|---|
| 2007/0211033 A1* | 9/2007 | Farag | G06F 3/03543 345/163 |
| 2008/0284735 A1* | 11/2008 | Shim | G06F 3/0317 345/166 |
| 2013/0113705 A1* | 5/2013 | Gu | G06F 3/03543 345/166 |

FOREIGN PATENT DOCUMENTS

JP      2008204388      9/2008

* cited by examiner

*Primary Examiner* — Sanjiv D. Patel
(74) *Attorney, Agent, or Firm* — JCIPRNET

(57) ABSTRACT

An input device configured to communicate with an information processing device includes a light source unit configured to emit light; a case including a first surface including a first opening and configured to emit the light toward a target object through the first opening, and a second surface including a second opening and configured to emit the light toward a living body through the second opening; a first light reception unit configured to receive first light from the target object through the first opening of the first surface; and a second light reception unit configured to receive second light from the living body through the second opening of the second surface.

12 Claims, 8 Drawing Sheets

INPUT DEVICE AND BIOMETRIC INFORMATION DETECTION DEVICE

The present application is based on, and claims priority from JP Application Serial Number 2023-039390, filed Mar. 14, 2023, the disclosure of which is hereby incorporated by reference herein in its entirety.

BACKGROUND

1. Technical Field

The present disclosure relates to an input device and a biometric information detection device.

2. Related Art

As an optical mouse, there hitherto has been proposed an optical mouse including a mode selection switch for performing selection between a mouse mode and a pulse measurement mode. In the mouse mode, a moving direction of the mouse and a position thereof are detected. In the pulse measurement mode, various types of biometric information (a pulse rate, a vascular age, and the like) are calculated.

However, an optical mouse disclosed in JP-A-2008-204388, it is difficult to acquire light from a mouse pad and light from a living body at the same time.

The optical mouse includes one opening portion through which light from a mouse pad or a finger is incident so that a light reception unit receives the light. As a result, the light from the living body cannot be received while receiving the light from the mouse pad, and the light from the mouse pad cannot be received while receive the light from the living body, which causes a problem. Thus, a mouse capable of detecting a moving direction of the mouse and biometric information at the same time has been required.

SUMMARY

According to one aspect of the present disclosure, provided is an input device configured to communicate with an information processing device, the input device including: a light source unit configured to emit light, a case including a first surface including a first opening and configured to emit the light toward a target object through the first opening, and a second surface including a second opening and configured to emit the light toward a living body through the second opening, a first light reception unit configured to receive first light from the target object through the first opening of the first surface, and a second light reception unit configured to receive second light from the living body through the second opening of the second surface.

According to one aspect of the present disclosure, provided is a biometric information detection device including the input device described above, and the information processing device configured to communicate with the input device, in which the input device is movably provided, and a control unit is provided, the control unit being configured to detect a moving direction of the input device, based on reception of the first light at the first light reception unit, and detect biometric information about a user, based on reception of the second light at the second light reception unit.

DESCRIPTION OF EMBODIMENTS

With reference to the drawings, an embodiment of the present disclosure is described.

Note that, in the following drawings, the dimensions of some components may be scaled differently for ease of understanding for the components.

First Embodiment

Figure 1:
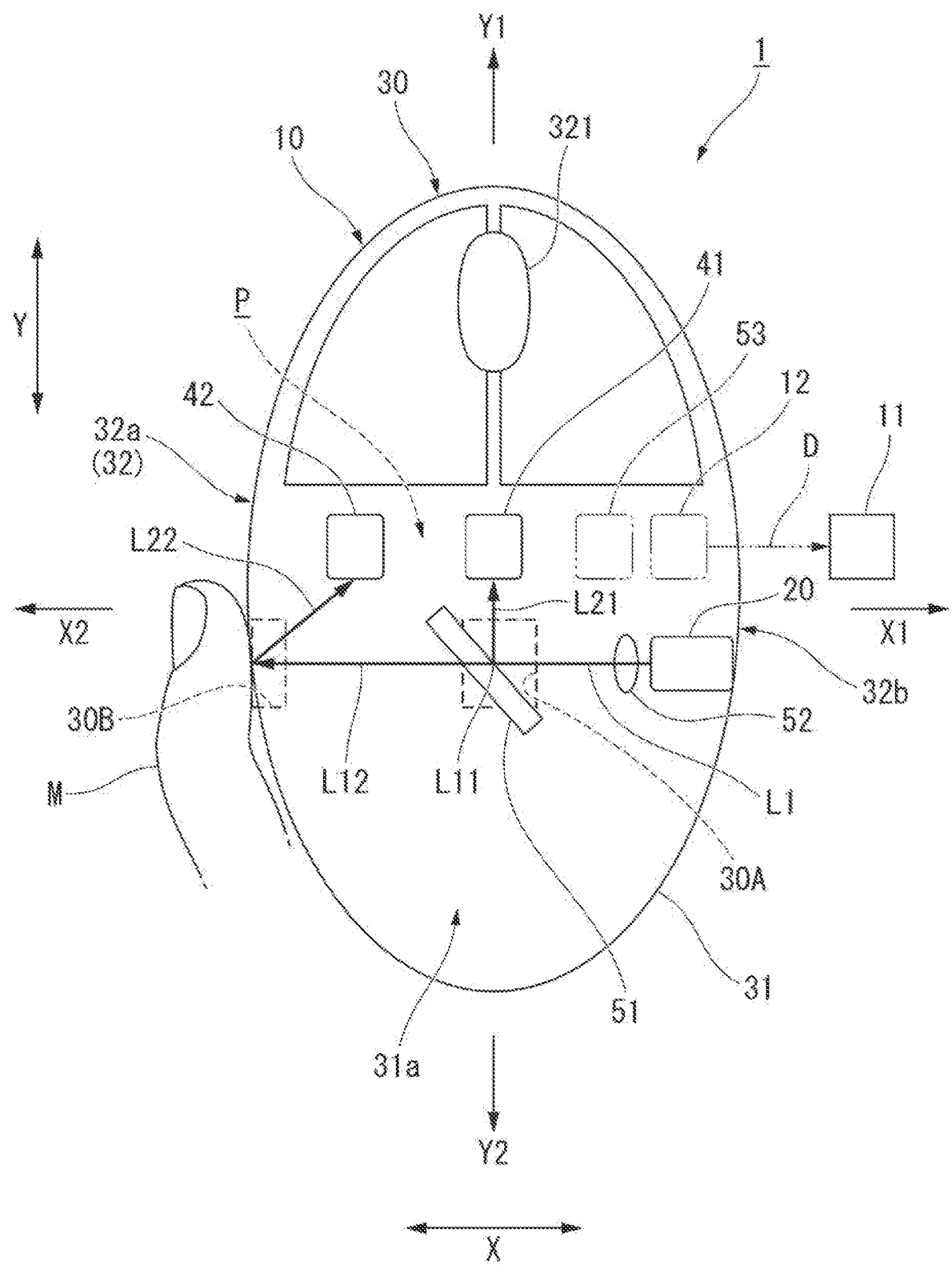
FIG. 1 is a plan view illustrating a schematic configuration of an optical mouse according to a first embodiment.
Figure 2:
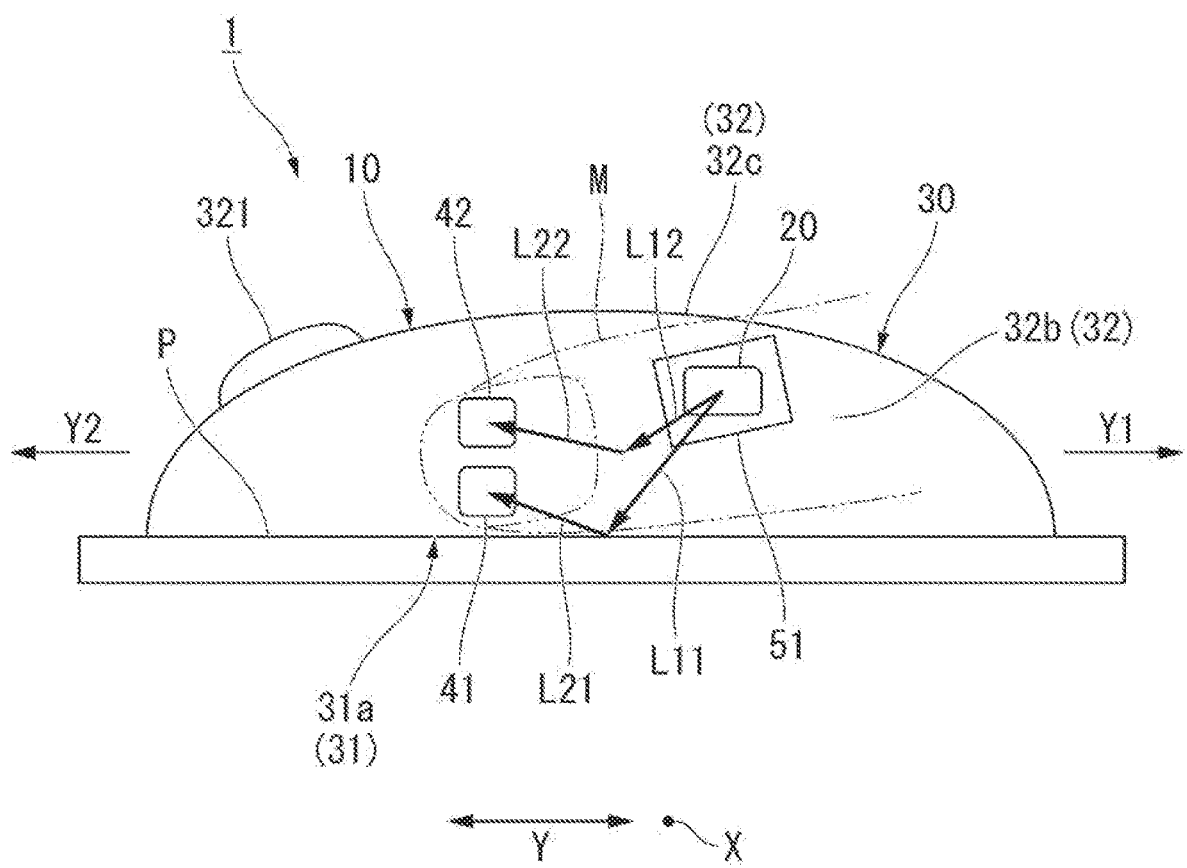
FIG. 2 is a cross-sectional view taken along a front-and-rear direction of a mouse main body of the optical mouse in FIG. 1.

As illustrated in FIG. 1 and FIG. 2, an optical mouse 1 (biometric information detection device) according to the first embodiment includes a mouse main body 10 (input device) capable of performing a function of detecting a moving direction and a position of the mouse itself, based on reflection light from a target object P (a normal mouse function) and a function of detecting biometric information D, based on reflection light from a living body M, at the same time during the use of the optical mouse 1.

The target object P is an upper surface of a mouse pad (omitted in illustration) on a desk, a top plate of a desk, or the like. The living body M is a fingertip (the first embodiment) or a palm of a hand (a modification example described later) of a user, or the like. Further, the biometric information D is biometric information about a user who uses the optical mouse 1, such as a pulse rate, a vascular age, or the like of a user.

The optical mouse 1 includes the mouse main body 10, an information processing device 11 that communicates with the mouse main body 10, and a control unit 12 that controls the mouse main body 10.

The mouse main body 10 is provided to be movable by an operation of a user. The mouse main body 10 includes a light source unit 20 that emits light L1, a case 30 that forms an outer shell of the mouse main body 10, and a pair of light reception units 41 and 42 that receive light obtained by reflecting the light L1 from the light source unit 20 by the target object P and the living body M, respectively.

Here, the case 30 of the mouse main body 10 is formed to have a substantially elliptical shape vertically elongated in a front-and-rear direction in plan view. The vertical direction is defined as a longitudinal direction Y, and the horizontal direction is defined as a short direction X. Note that the direction in the short direction X may also be referred to as a right-and-left direction. In plan view in the right-and-left direction, the right side is denoted with a reference sign X1, and the left side is denoted with a reference sign X2.

The case 30 includes a lower case unit 31 including a lower surface 31a (first surface) and an upper case unit 32 including a right surface 32b on one end side in the short direction X (the right side X1 in the present embodiment), a left surface 32a (second surface) on the other end side in the short direction X (the left side X2 in the present embodiment), and an upper surface 32c. The upper case unit 32 is provided to cover the lower surface 31a of the lower case unit 31. The upper case unit 32 includes a movable portion 321 being movable at substantially the center portion in the short direction X on one end side (front side Y1) in the longitudinal direction Y.

Figure 3:
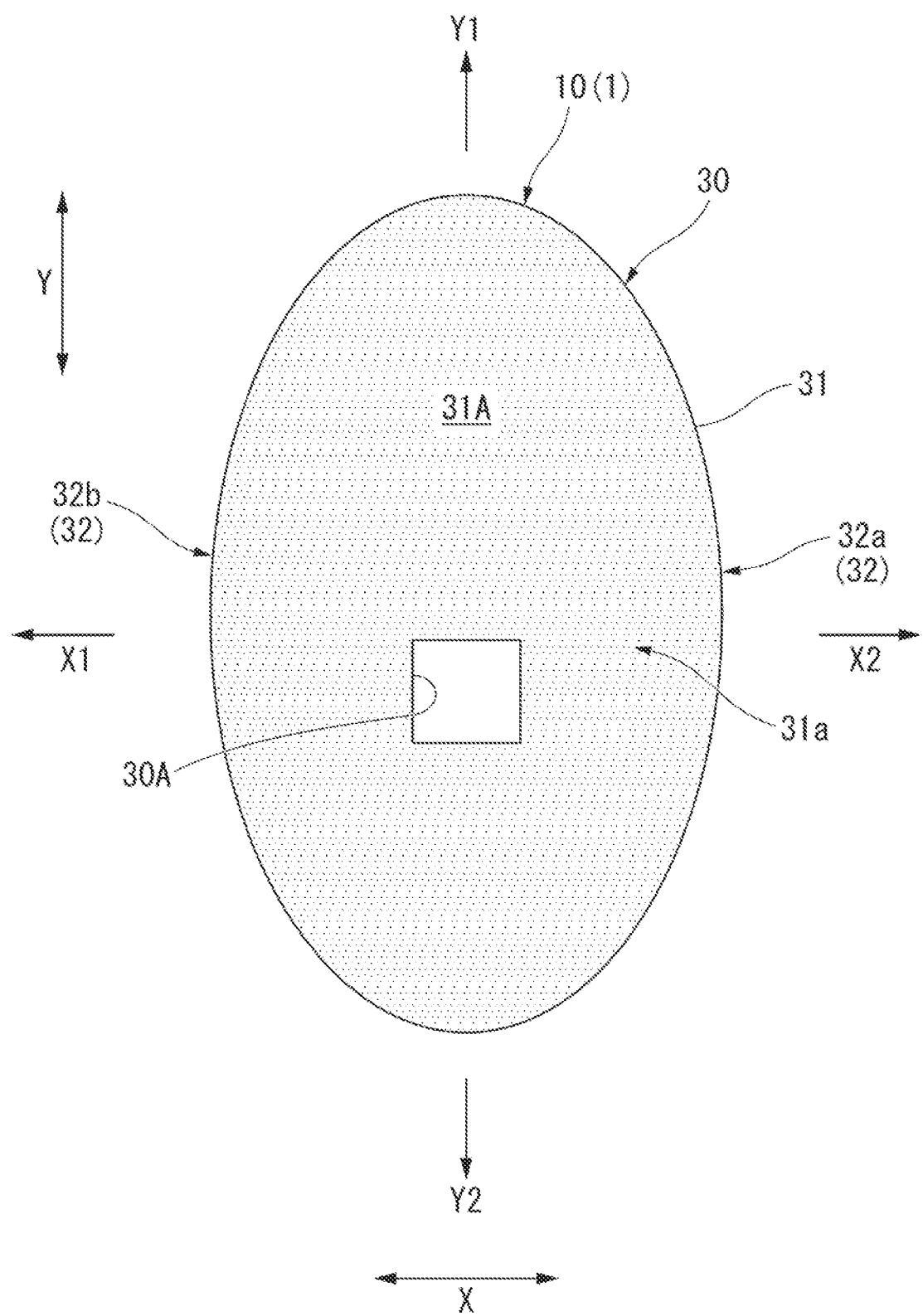
FIG. 3 is a diagram illustrating a lower surface of the mouse main body.

The lower surface 31a includes a first opening 30A, and is a surface from which the light L1 is emitted toward the target object P through the first opening 30A. The lower surface 31a is a surface of the case 30 that comes into contact with the target object P and does not come into contact with the living body M. The lower surface 31a is a flat surface including the longitudinal direction Y and the short direction X. As illustrated in FIG. 3, the range of the lower surface 31a matches with a first region 31A facing the target object P.

The first opening 30A is only required to be arranged in the first region 31A. In the present embodiment, the first opening 30A is arranged at the center of the lower surface 31a in the short direction X, slightly towards the rear side Y2 (user side, front side) with respect to the center in the longitudinal direction Y. The first opening 30A has a rectangular shape as viewed from the lower surface side. Note that the size and the shape of the first opening 30A may be set freely.

Figure 4:
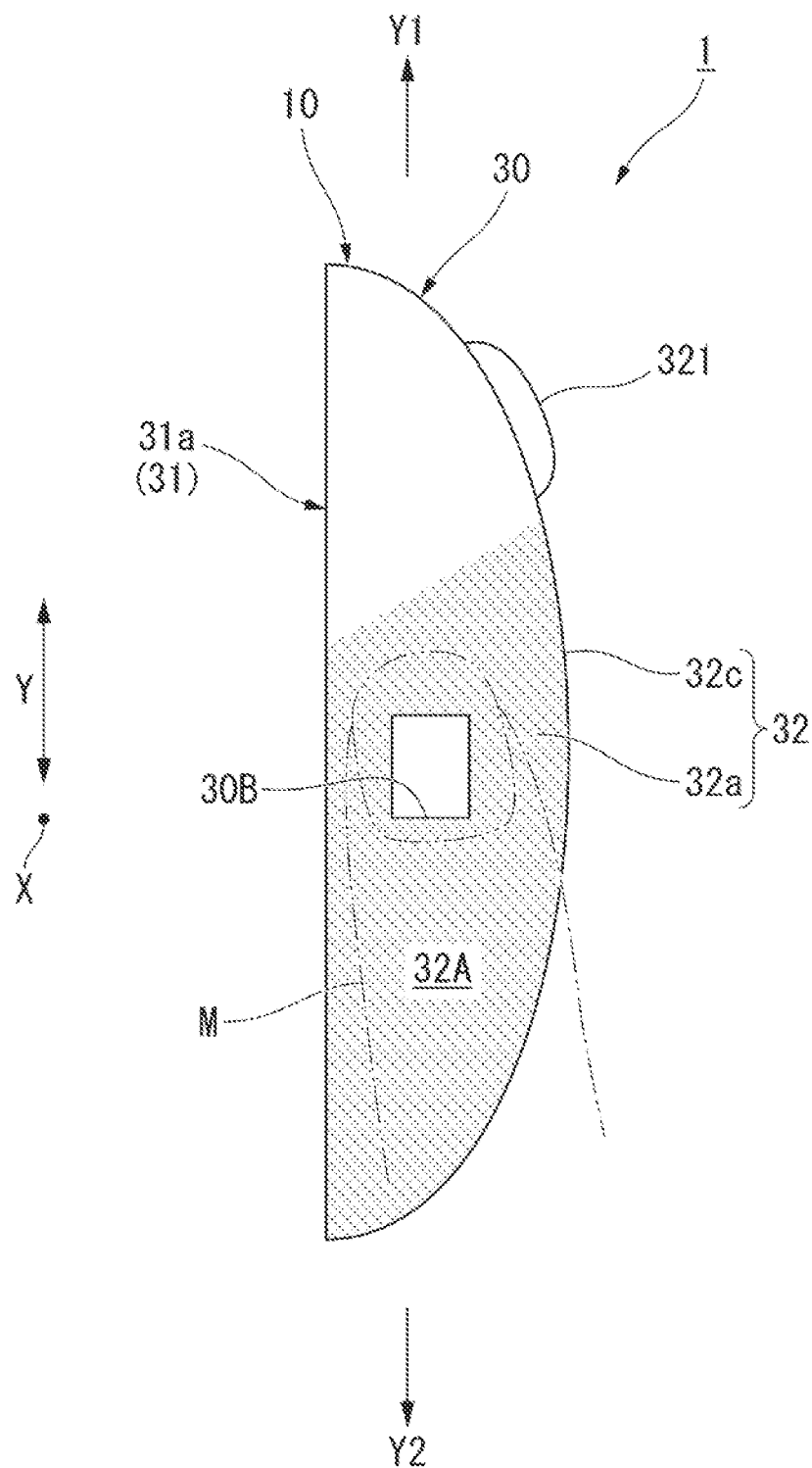
FIG. 4 is a side view of the mouse main body as viewed from the left side.

The left surface 32a includes a second opening 30B, and is a surface from which the light L1 is emitted toward the living body M through the second opening 30B. The left surface 32a is a surface of the case 30 that comes into contact with the living body M and does not come into contact with the target object P. The left surface 32a forms a protruding curved surface that protrudes to the left side X2 at the center in the longitudinal direction in plan view. Note that the shape of the left surface 32a may be set freely in accordance with usability for a user. The shape of the right surface 32b is also set freely. As illustrated in FIG. 4, the left surface 32a includes a second region 32A with which a thumb (the living body M) overlaps when a user holds the case 30 with the right hand.

The second opening 30B is only required to be arranged in the second region 32A. In the present embodiment, the second opening 30B is arranged at the center of the left surface 32a in the longitudinal direction Y and the center in the up-and-down direction. In other words, the second opening 30B is provided at a position covered with a hand or a finger of a user who uses the mouse and holds the mouse main body 10. The second opening 30B has a rectangular shape as viewed from the lower surface side. Note that the size and the shape of the second opening 30B may be set freely.

As illustrated in FIG. 1, the mouse main body 10 includes, in the case 30, the light source unit 20 described above, the pair of openings described above (the first opening 30A and the second opening 30B), the first light reception unit 41 corresponding to the first opening 30A, the second light reception unit 42 corresponding to the second opening 30B, a deflection mirror 51 (deflection unit) arranged between the light source unit 20 and each of the pair of openings 30A and 30B, and a condensing lens 52 (optical member) provided between the light source unit 20 and the deflection mirror 51.

The light source unit 20 includes a light-emitting diode. The light L1 from the light source unit 20 is emitted toward the deflection mirror 51. The condensing lens 52 condenses the light L1 from the light source unit 20 so that the light L1 arrives at the deflection mirror 51.

As the deflection mirror 51, a half mirror is adopted. The deflection mirror 51 deflects first light L11, which is one part of the emission light L1 emitted from the light source unit 20, toward the first opening 30A provided in the lower surface 31a of the lower case unit 31, and transmits second light L12, which is another part of the emission light L1, and emits the second light L12 toward the second opening 30B provided in the left surface 32a of the upper case unit 32. The first light L11 reflected and deflected by the deflection mirror 51 is reflected by the target object P through the first opening 30A, and then first reflection light L21 thus generated is incident on the first light reception unit 41. The second light L12 transmitted through the deflection mirror 51 is reflected by the living body M (a finger of a user who uses the mouse main body 10) through the second opening 30B, and then second reflection light L22 thus generated is incident on the second light reception unit 42.

Orientation (deflection angle) of the deflection mirror 51 is set in accordance with conditions such as a position of the light source unit 20, an incident angle of the emission light L1, orientation of the first light L11 to be deflected, and orientation of the second light L12 to be transmitted.

The first light reception unit 41 receives the first reflection light L21 from the target object P through the first opening 30A of the lower surface 31a of the lower case unit 31. The second light reception unit 42 receives the second reflection light L22 from the living body M through the second opening 30B of the left surface 32a of the upper case unit 32.

The control unit 12 is provided in the case 30. The control unit 12 performs control for detecting the moving direction and the present position of the mouse main body 10 itself, based on a speckle pattern of the first reflection light L21 incident on the first light reception unit 41, and control for detecting the biometric information D such as a blood oxygenation level or the like of a user by using intensity of the second reflection light L22 incident on the second light reception unit 42. When the second light reception unit 42 receives the second reflection light L22, the control unit 12 performs control so that the moving direction and the current position of the mouse main body 10 is detected based on reception of the first reflection light L21 by the first light reception unit 41. At the same time, the control unit 12 performs control so that the biometric information D is detected based on reception of the second reflection light L22 by the second light reception unit 42.

Further, when the first light reception unit 41 receives the first reflection light L21, and the second light reception unit 42 does not receive the second reflection light L22, the control unit 12 performs control for turning off the power of the optical mouse 1 so as to prevent the light source unit 20 from emitting the emission light L1. When the optical mouse 1 is not in use, and the power is in an ON state, such control can prevent leakage of the emission light L1 (the second light L12), which is emitted from the light source unit 20 and is not reflected by a finger closing the second opening 30B, to the outside.

Further, the control unit 12 transmits information relating to the biometric information D about the user, which is detected by the second reflection light L22 received by the second light reception unit 42, to the information processing device 11. The information processing device 11 is provided outside of the mouse main body 10. In the information processing device 11, processing is executed as appropriate, such as accumulation or display of the biometric information D received from the control unit 12.

Further, the mouse main body 10 includes an acceleration sensor 53 (detection member) that detects movement of the mouse main body 10. The acceleration sensor 53 is embedded in the case 30.

In the optical mouse 1 thus configured, when the power of the mouse main body 10 is turned on, the emission light L1 is emitted from the light source unit 20. When the second light reception unit 42 does not receive the second reflection light L22, the control unit 12 turned off the power to stop emission of the emission light L1 from the light source unit 20. When the second light reception unit 42 receives the second reflection light L22, control is performed so that the moving direction and the current position of the mouse main body 10 is detected based on reception of the first reflection light L21 by the first light reception unit 41. At the same time, control is performed so that the biometric information D is detected based on reception of the second reflection light L22 by the second light reception unit 42.

Further, when the acceleration sensor 53 detects movement of the mouse main body 10, the control unit 12 performs control for detecting the biometric information D about the user, based on the second reflection light L22 received by the second light reception unit 42. After that, in a stet in which the biometric information D is detected by receiving the light by the second light reception unit 42, control is performed so that a heart rate sensor (PPG sensor) or the like provided to the control unit 12, which is omitted in illustration, is continuously turned ON and the PPG sensor is turned OFF when the biometric information D is not detected.

The biometric information D detected by the control unit 12 is transmitted to the information processing device 11 provided to the outside of the mouse main body 10. Then, the information processing device 11 subjects the received biometric information D to data processing as appropriate. In other words, the biometric information D received from the control unit 12 is monitored through, for example, display by a monitor of a personal computer or a mobile terminal, which is omitted in illustration. With this, a physical condition of a user can be recognized. For example, fluctuations or cessation in a pulse wave of a user, vessel constriction due to excessing stress, or the like can be monitored in real time, which enables proactive measures for prevention.

Next, actions of the mouse main body 10 and the optical mouse 1 are described.

As illustrated in FIG. 1, the mouse main body 10 according to the present embodiment communicates with the information processing device 11. The mouse main body 10 includes the light source unit 20 that emits the emission light L1, the case 30 that includes the lower surface 31*a* including the first opening 30A and that emits the light toward the target object P through the first opening 30A, and the left surface 32*a* including the second opening 30B and that emits the light toward the living body M through the second opening 30B, the first light reception unit 41 that receives the first reflection light L21 from the target object P through the first opening 30A of the lower surface 31*a*, and the second light reception unit 42 that receives the second reflection light L22 from the living body M through the second opening 30B of the left surface 32*a*.

Therefore, in the present embodiment, the emission light L1 emitted from the light source unit 20 can be reflected by the target object P and the living body M through the first opening 30A and the second opening 30B, respectively. In the present embodiment, the first opening 30A through which the target object P is irradiated with the first light L11 and the second opening 30B through which the living body M is irradiated with the second light L12 are provided. Thus, there is no need to perform switching between detection of the target object P and detection of the living body M. The reflection light L21 and the reflection light L22 obtained by irradiating both the objects (the target object P and the living body M) with the light L1 and capturing its reflection therefrom are received by the first light reception unit 41 and the second light reception unit 42, respectively at the same time. The moving direction and the position of the mouse main body 10 can be detected from the target object P, and the biometric information D about the user can be detected from the living body M, at the same time. In other words, even when the second light reception unit 42 receives the second reflection light L22, the first light reception unit 41 is capable of receiving the first reflection light L21.

Further, in the present embodiment, the mouse main body 10 is communicable with the information processing device 11. Thus, the biometric information D acquired by the mouse main body 10 can be transmitted to the information processing device 11. Then, processing can be executed as appropriate, such as display of the acquired biometric information D on a terminal, accumulation of the data, and comparison.

Further, in the present embodiment, the deflection mirror 51 is included. The deflection mirror 51 deflects one part of the emission light L1 (the first light L11), and transmits another part of the emission light L1 (the second light L12). The deflection mirror 51 deflects the first light L11 toward the first opening 30A of the lower surface 31*a*, and transmits the second light L12 toward the second opening 30B of the left surface 32*a*. In this case, the deflection mirror 51 is used. With this, one emission light L1 can be formed into the two parts of light (the first light L11 and the second light L12) advancing to the target object P and the living body M, respectively. With this simple configuration, the moving direction of the mouse main body 10 and the biometric information D can be detected at the same time.

In the mouse main body 10 according to in the present embodiment, the lower surface 31*a* is a surface of the case 30 that comes into contact with the target object P and does not come into contact with the living body M. The left surface 32*a* is a surface of the case 30 that comes into contact with the living body M and does not come into contact with the target object P. In this case, the lower surface 31*a* that comes into contact with the target object P and includes the first opening 30A and the left surface 32*a* that comes into contact with the living body M and includes the second opening 30B are different surfaces, and do not come into contact with the targets (the target object P and the living body M) that are not detected by the respective surfaces. With this, detection can be performed at high accuracy.

In the mouse main body 10 according to the present embodiment, the case 30 includes the lower case unit 31 including the lower surface 31*a* and the upper case unit 32 covering the lower surface 31*a* and including the left surface 32*a*. The upper case unit 32 includes the left surface 32*a* at the one end side of the case 30 in the short direction X. In this case, the second opening 30B can be formed in the left surface 32*a* of the upper case unit 32. Thus, when a user holds and uses the mouse main body 10, a finger of the user is placed on the second opening 30B. With this, the biometric information D can be detected from the finger.

The mouse main body 10 according to the present embodiment includes the condensing lens 52 between the light source unit 20 and the deflection mirror 51. In this case, the emission light L1 emitted from the light source unit 20 can be condensed by the condensing lens 52, and can be incident on the deflection mirror 51. In other words, the emission light L1 can be efficiently incident on the deflection mirror 51 without a loss, which is effective in the present embodiment where the deflection mirror 51 deflects one part of the light, and transmits another part of the light.

The optical mouse 1 according to the present embodiment includes the mouse main body 10 described above and the information processing device 11 that communicates with the mouse main body 10. The mouse main body 10 is provided to be movable. The control unit 12 is included. The control unit 12 detects the moving direction of the mouse main body 10, based on reception of the first reflection light L21 by the first light reception unit 41, and detects the biometric information D about the user, based on reception of the second reflection light L22 by the second light reception unit 42. In this case, the control unit 12 is capable of controlling detection timing for the moving direction and the position of the mouse main body 10 and the biometric information D, the ON/OFF states, and the like in accordance with the light reception states of the first light reception unit 41 and the second light reception unit 42.

With the optical mouse 1 according to the present embodiment, when the second light reception unit 42 receives the second reflection light L22, the control unit 12 detects the moving direction of the mouse main body 10, based on reception of the first reflection light L21 by the first light reception unit 41. In this case, when the second light reception unit 42 does not receive the second reflection light L22, the living body M is not located on the second opening 30B, in other words, a user does not operate the mouse main body 10. Thus, the control unit 12 is capable of performing control for stopping detection the moving direction and the position of the mouse main body 10 by the first light reception unit 41.

Further, in the present embodiment, the control unit 12 transmits the information relating to the biometric information D about the user to the information processing device 11. In this case, the information processing device 11 can execute processing as appropriate, such as display the biometric information D, which is received and acquired from the mouse main body 10, on a terminal, accumulation of the data, and comparison.

Further, in the present embodiment, the acceleration sensor 53 that detects movement of the mouse main body 10 is included. When the acceleration sensor 53 detects movement of the mouse main body 10, the control unit 12 detects the biometric information D about the user, based on reception of the second reflection light L22 by the second light reception unit 42. In this case, the biometric information D can be acquired only when the acceleration sensor 53 recognizes movement of the mouse main body 10. Thus, when the mouse main body 10 does not move, the mouse main body 10 is not operated, and hence emission of the second light L12 from the second opening 30B to the outside can be suppressed.

According to at least one embodiment described above, the moving direction of the mouse main body 10 and the biometric information D can be detected at the same time.

First Modification Example

Figure 5:
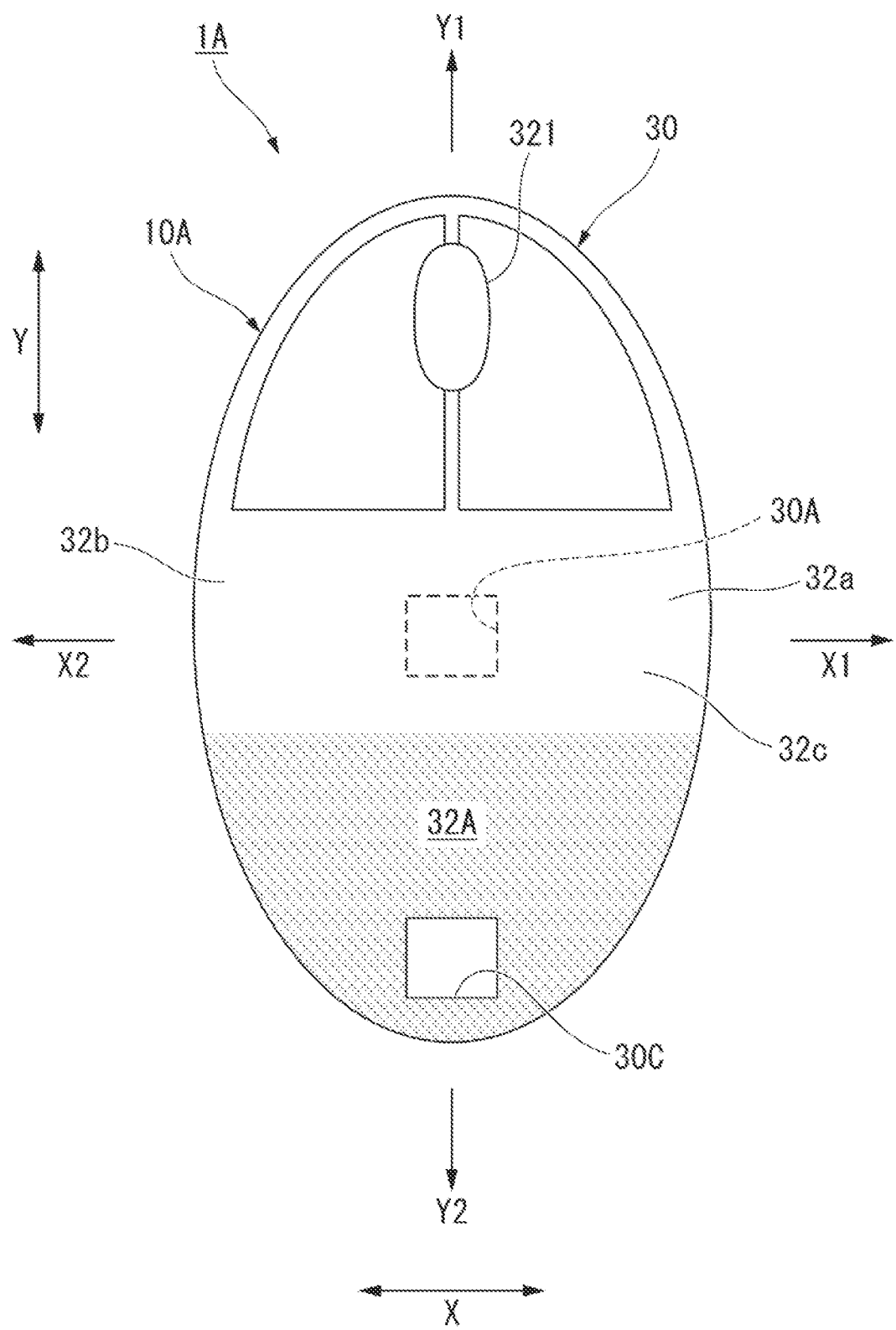
FIG. 5 is a plan view of a mouse main body in a first modification example of the first embodiment.

FIG. 5 is a plan view of a mouse main body 10A of an optical mouse 1A (biometric information detection device) in a first modification example of the first embodiment.

As illustrated in FIG. 5, in the first modification example, the case 30 of the mouse main body 10A includes the lower case unit 31 including the lower surface 31a and the upper case unit 32 covering the lower surface 31a and including the upper surface 32c (second surface). The upper surface 32c of the upper case unit 32 is provided with a second opening 30C at the center in the short direction X on the rear side Y2 in the longitudinal direction Y. The second opening 30C is located in a region of the upper surface 32c that is covered with a palm of a hand of a user. In the present modification example, similarly to the first embodiment described above, the second light transmitted through the deflection mirror is also reflected by a living body (a palm of a hand of a user) through the second opening 30C, and then the second reflection light thus generated is also incident on the second light reception unit.

In the present modification example, a user who uses the mouse main body 10A can operate the mouse main body 10A whether the user is right-handed or left-handed, and biometric information about the user can be detected. In other words, similarly to the first embodiment described above, in a case in which the second opening 30B is provided in the left surface 32a (see FIG. 1), when the mouse main body 10 is operated by a left hand, a finger (living body) may not be placed at the position of the second opening 30B. However, in the present modification example, the mouse main body 10A may be held by any one of a right hand and a left hand, and hence has advantageous usability.

Second Embodiment

Figure 6:
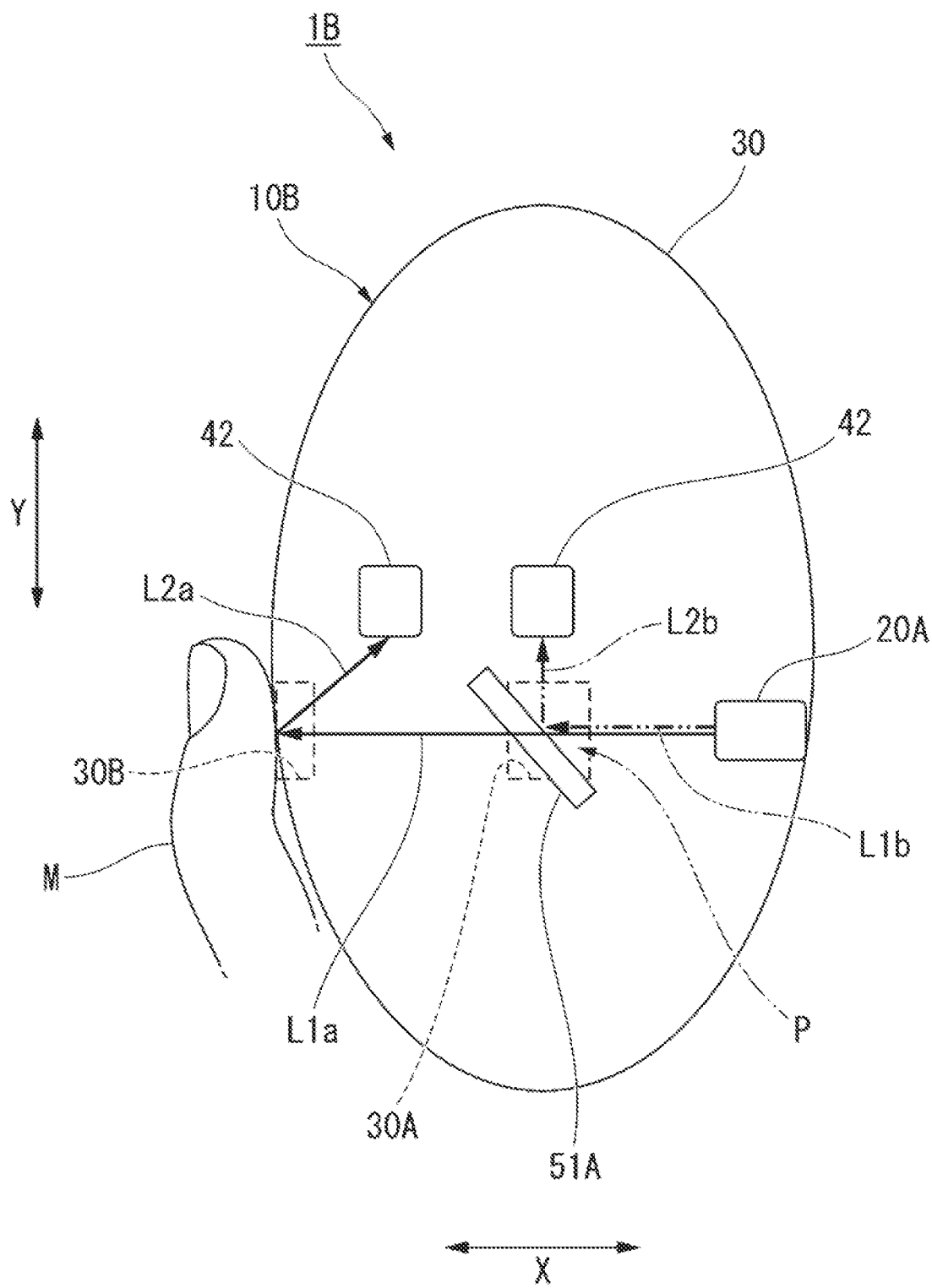
FIG. 6 is a plan view illustrating a schematic configuration of a mouse main body of an optical mouse according to a second embodiment.

FIG. 6 is a plan view illustrating an internal structure of a mouse main body 10B of an optical mouse 1B (biometric information detection device) according to a second embodiment.

As illustrated in FIG. 6, in the mouse main body 10B according to the second embodiment, emission light emitted from a light source unit 20A includes light having a first wavelength (red light L1a) and light having a second wavelength being a wavelength different from the first wavelength (blue light L1b). The second wavelength of the blue light L1b is shorter than the first wavelength of the red light L1a. For example, the wavelength band of the first wavelength of the red light L1a is near 620 nm with a red emission color, and the wavelength band of the second wavelength of the blue light L1b is near 460 nm with a blue emission color. In other words, the light source unit 20A according to the second embodiment emits the light with the two emission colors of red and blue.

A deflection mirror 51A (deflection unit) according to the second embodiment deflects the blue light L1b toward the target object, and deflects the red light L1a toward the living body. The red light L1a is deflected toward the second opening 30B by the deflection mirror 51A. The red light L1a is reflected by the living body, and the reflection light thus generated (red reflection light L2a) is incident on the second light reception unit 42. The blue light L1b is deflected toward the first opening 30A by the deflection mirror 51A. The blue light L1b is reflected by the target object, and the reflection light thus generated (blue reflection light L2b) is incident on the first light reception unit 41.

In this manner, the deflection mirror 51A according to the second embodiment is configured by a diffraction element that diffracts light, in place of the half mirror in the first embodiment. The deflection mirror 51A is arranged obliquely at an appropriate angle with respect to the red light L1a and the blue light L1b that are emitted from the light source unit 20A.

Note that, in the second embodiment, there is adopted a configuration in which one light source unit 20A is provided. However, a configuration in which a plurality of light source units that respectively emit the two parts of light L1a and L1b are provided may be adopted. In other words, a light source unit that emits the blue light L1b for detecting the moving direction of the mouse main body 10B and a light source unit that emits the red light L1a for detecting biometric information about a user may be provided.

According to the second embodiment, the two types of light (the red light L1a and the blue light L1b) can be used, and the respective light can be deflected to the first opening 30A and the second opening 30B by the deflection mirror 51A. The different types of light are separately adopted, and hence the light can be securely reflected by the target object P and the living body M and received by the light reception units 41 and 42.

Third Embodiment

Figure 7:
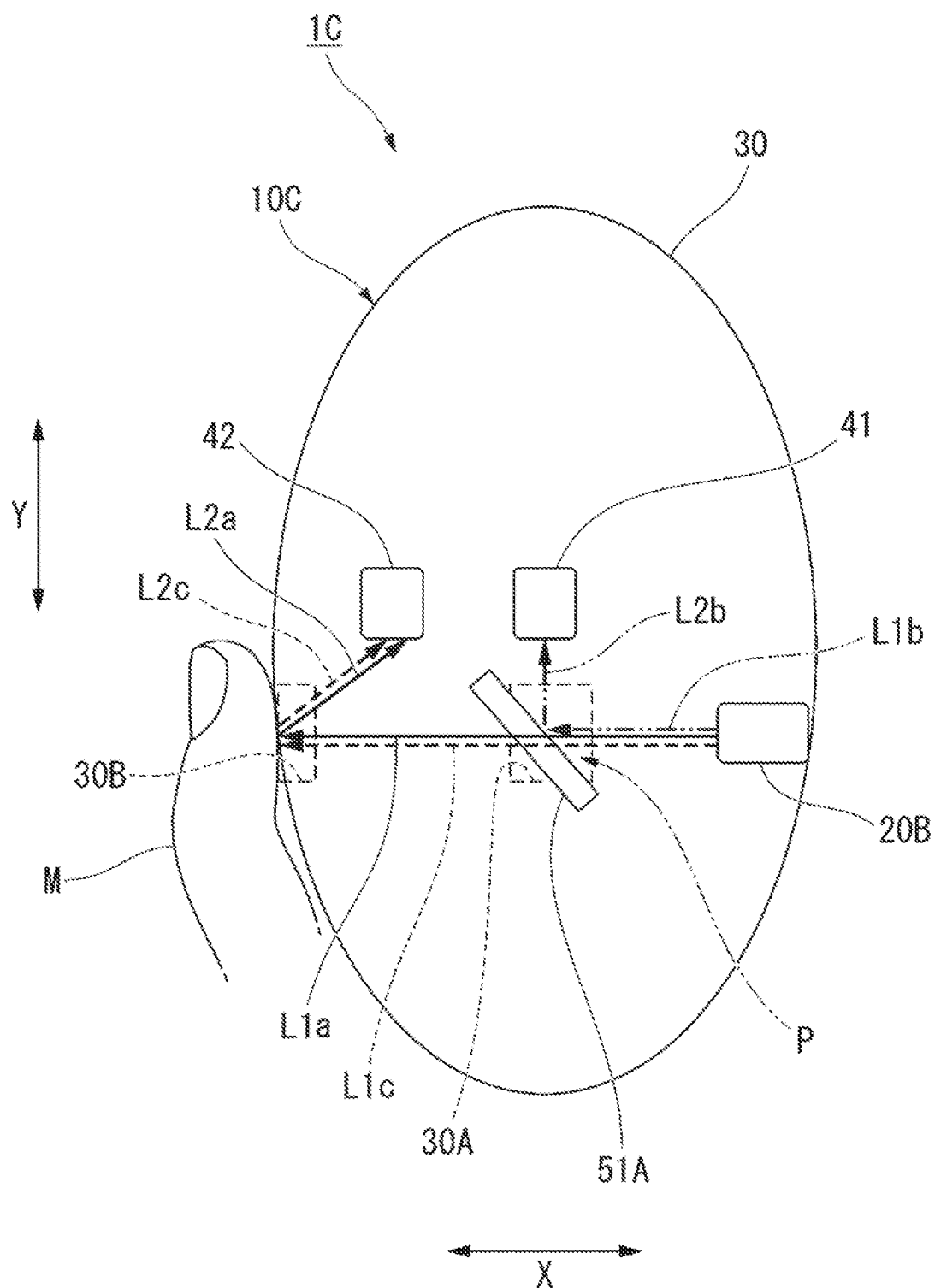
FIG. 7 is a plan view illustrating a schematic configuration of a mouse main body of an optical mouse according to a third embodiment.

FIG. 7 is a plan view illustrating an internal structure of a mouse main body 10C of an optical mouse 1C according to a third embodiment.

In the mouse main body 10C according to the third embodiment, the two parts of light having different wavelengths are incident on the second opening 30B and the second light reception unit 42 in the configuration of the second embodiment described above. As illustrated in FIG. 7, in the mouse main body 10C according to the third embodiment, emission light from a light source unit 20B includes the light having the first wavelength (the red light L1a), the light having the second wavelength (the blue light L1b), and light having a third wavelength (green light L1c), which have wavelengths different from one another.

The second wavelength of the blue light L1b is shorter than the first wavelength of the red light L1a and the third wavelength of the green light L1c. The third wavelength of the green light L1c is longer than the first wavelength of the red light L1a. For example, the wavelength band of the first wavelength of the red light L1a is near 620 nm with a red emission color, the wavelength band of the second wavelength of the blue light L1b is near 460 nm with a blue emission color, and the wavelength band of the third wavelength of the green light L1c is near 530 nm with a green emission color. For example, the wavelength band of the second wavelength of the blue light Lib is near 530 nm with a green emission color, the wavelength band of the first wavelength of the red light L1a is near 620 nm with a red emission color, and the wavelength band of the third wavelength of the green light L1c is near 530 nm with a green emission color. In other words, the light source unit 20B according to the third embodiment emit the light with the three colors of red, blue, and green.

The deflection mirror 51A (deflection unit) according to the third embodiment deflects the blue light L1b toward the target object P, and deflects the red light L1a and the green light L1c toward the living body M. Each of the red light L1a and the green light L1c is deflected toward the second opening 30B by the deflection mirror 51A. The red light L1a and the green light L1c are reflected respectively by the living body M, and the reflection light thus generated (the red reflection light L2a and the green reflection light L2c) are incident on the second light reception unit 42. The blue light L1b is deflected toward the first opening 30A by the deflection mirror 51A. The blue light L1b is reflected by the target object P, and the reflection light thus generated (blue reflection light L2b) is incident on the first light reception unit 41.

In this manner, the deflection mirror 51A according to the third embodiment is configured by a diffraction element that diffracts light, in place of the half mirror in the first embodiment. The deflection mirror 51A is arranged obliquely at an appropriate angle with respect to the red light L1a, the blue light L1b, and the green light L1c that are emitted from the light source unit 20B.

Figure 8:
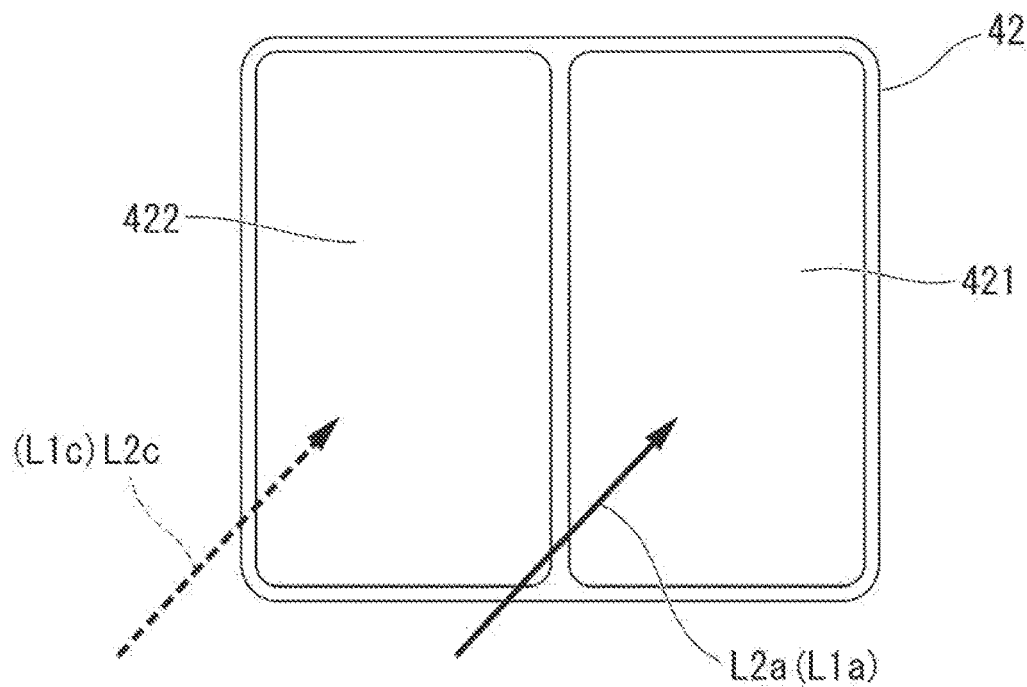
FIG. 8 is a diagram illustrating a configuration of a second light reception unit of the mouse main body illustrated in FIG. 7.

Further, as illustrated in FIG. 8, the second light reception unit 42 includes a first light reception member 421 that receives the red reflection light L2a obtained by reflecting the red light L1a having the first wavelength and a second light reception member 422 that receives the green reflection light L2c obtained by reflecting the green light L1c having the third wavelength.

Note that, in the third embodiment, there is adopted a configuration in which one light source unit 20B is provided. However, a configuration in which a plurality of light source units that respectively emit the three parts of light L1a, L1b, and L1c are provided may be adopted. In other words, a light source unit that emits the blue light L1b for detecting the moving direction of the mouse main body 10C and light source units that emit the red light L1a and the green light L1c for detecting biometric information about a user may be provided.

According to the third embodiment, the two types of light having different wavelengths (the red light L1a and the green light L1c) can be reflected by the living body M through the second opening 30B, and the red reflection light L2a and the green reflection light L2c can separately be received by the first light reception member 421 and the second light reception member 422, respectively. Thus, the two types of biometric information D can be detected efficiently.

Second Modification Example

Figure 9:
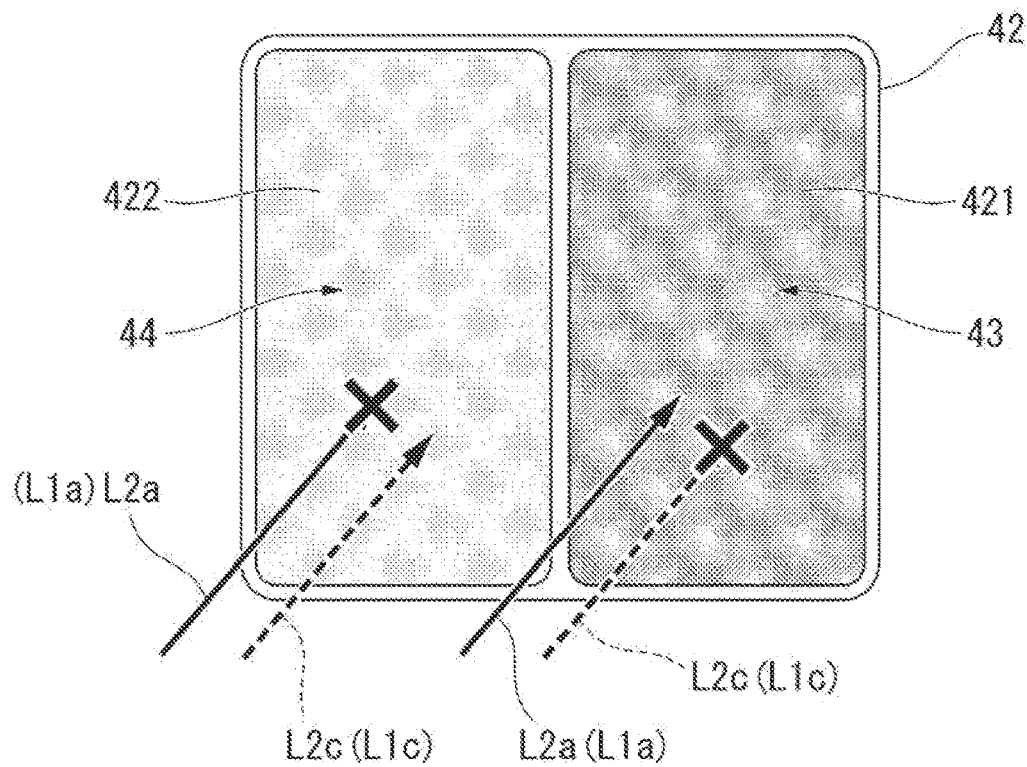
FIG. 9 is a diagram illustrating a configuration of a second light reception unit of a mouse main body in a second modification example of the third embodiment.

A second modification example illustrated in FIG. 9 is a configuration obtained by changing the configuration of the second light reception unit 42 in the third embodiment described above. The second light reception unit 42 includes the first light reception member 421 that receives the red light L1a having the first wavelength (the red reflection light L2a) and the second light reception member 422 that receives the green light L1c having the third wavelength (the green reflection light L2c).

The first light reception member 421 includes a first color filter 43 that transmits the red light L1a having the first wavelength (the red reflection light L2a) blocks the blue light L1b having the second wavelength (the blue reflection light L2b) and the green light L1c having the third wavelength (the green reflection light L2c), which are illustrated in FIG. 7. The second light reception member 422 includes a second color filter 44 that transmits the green light L1c having the third wavelength (the green reflection light L2c) and blocks the red light L1a having the first wavelength (the red reflection light L2a) and the blue light L1b having the second wavelength (the blue reflection light L2b).

In the second modification example, the first light reception member 421 including the first color filter 43 can only receive the red reflection light L2a while blocking the green reflection light L2c. The second light reception member 422 including the second color filter 44 can only receive the green reflection light L2c while blocking the red reflection light L2a.

Some of the embodiments of the present disclosure are described above. However, those embodiments are given merely as examples, and are not intended to limit the scope of the present disclosure. Those embodiments can be carried out in various other forms, and various omission, replacement, and modifications may be made thereto without departing from the gist of the present disclosure. Those embodiments and the modifications thereof are within the scope and the gist of the present disclosure, and are also encompassed within the scope of claims and the scope of the equivalents in the present disclosure.

In the first embodiment described above, there is adopted a configuration in which the moving direction of the mouse main body 10 is detected by using the reflection light reflected by the deflection mirror 51 constituted by a half mirror and the biometric information D about the user is detected by using the light transmitted through the deflection mirror 51. However, the configuration is not limited thereto. There may be adopted a configuration in which the moving direction of the mouse main body 10 is detected by using the light transmitted through the deflection mirror 51 and the biometric information D about the user is detected by using the light reflected by the deflection mirror 51.

In the optical mouse 1 (biometric information detection device), the configuration such as a position, orientation, and a shape of each of the components including the light source unit, the detecting unit, the light reception unit, and each of the openings is not limited to the embodiments described above, and may be set as appropriate. That is, it is only required to provide the first opening and the first light reception unit for reflecting the light by the target object P and the second opening and the second light reception unit for reflecting the light by the living body M.

Further, in the present embodiment, the case 30 is provided with the lower case unit 31 including the first surface and the upper case unit 32 including the second surface, but the configuration thereof is not limited thereto.

Further, the control unit 12 may be omitted.

The input device according to one aspect of the present disclosure may include the following configuration.

The input device according to one aspect of the present disclosure is configured to communicate with an information processing device, and includes a light source unit configured to emit light, a case including a first surface including a first opening and configured to emit the light toward a target object through the first opening, and a second surface including a second opening and configured to emit the light toward a living body through the second opening, a first light reception unit configured to receive first light from the target object through the first opening of the first surface, and a second light reception unit configured to receive second light from the living body through the second opening of the second surface.

The input device according to one aspect of the present disclosure may include a deflection unit configured to deflect one part of the light and transmit another part of the light, in which the deflection unit may deflect the one part of the light emitted from the light source unit toward the first opening of the first surface and transmit the another part of the light emitted from the light source unit toward the second opening of the second surface.

In the input device according to one aspect of the present disclosure, the first surface may be a surface of the case that comes into contact with the target object and does not come into contact with the living body, and the second surface may be a surface of the case that comes into contact with the living body and does not come into contact with the target object.

In the input device according to one aspect of the present disclosure, the case may include a lower case unit including the first surface and an upper case unit covering the first surface and including the second surface, and the upper case unit may include the second surface at one end side of the case in a short direction.

In the input device according to one aspect of the present disclosure, the case may include a lower case unit including the first surface and an upper case unit covering the first surface and including the second surface, and the upper case unit may include a movable portion being movable at one end side of the case in a longitudinal direction and the second surface at the other end side in the longitudinal direction.

The input device according to one aspect of the present disclosure may include an optical member between the light source unit and the deflection unit.

In the input device according to one aspect of the present disclosure, the optical member may be a condensing lens.

In the input device according to one aspect of the present disclosure, the light emitted from the light source unit may include light having a first wavelength and light having a second wavelength different from the first wavelength, and the deflection unit may deflect the light having the second wavelength toward the target object and deflect the light having the first wavelength toward the living body.

In the input device according to one aspect of the present disclosure, the second wavelength may be shorter than the first wavelength.

In the input device according to one aspect of the present disclosure, the light emitted from the light source unit may include light having a third wavelength longer than the first wavelength, the deflection unit may deflect the light having the third wavelength toward the living body, and the second light reception unit may include a first light reception member configured to receive the light having the first wavelength and a second light reception member configured to receive the light having the third wavelength.

In the input device according to one aspect of the present disclosure, the first light reception member may include a first color filter that transmits the light having the first wavelength and blocks the light having the second wavelength and the light having the third wavelength, and the second light reception member may include a second color filter that transmits the light having the third wavelength and blocks the light having the first wavelength and the light having the second wavelength.

The biometric information detection device according to one aspect of the present disclosure may include the following configuration.

The biometric information detection device according to one aspect of the present disclosure includes the input device according to the above-mentioned aspect, the information processing device configured to communicate with the input device, in which the input device is movably provided, and a control unit is provided, the control unit being configured to detect a moving direction of the input device, based on reception of the first light at the first light reception unit, and detect biometric information about a user, based on reception of the second light at the second light reception unit.

In the biometric information detection device according to one aspect of the present disclosure, when the second light reception unit receives the second light, the control unit may detect the moving direction of the input device, based on reception of the first light at the first light reception unit.

In the biometric information detection device according to one aspect of the present disclosure, the control unit may transmit information relating to the biometric information about the user to the information processing device.

The biometric information detection device according to one aspect of the present disclosure may include a detection member configured to detect movement of the input device, and when the detection member detects movement of the input device, the control unit may detect the biometric information about the user, based on reception of the second light at the second light reception unit.

What is claimed is:

1. An input device configured to communicate with an information processing device, the input device comprising:
    a light source unit configured to emit light;
    a case including:
        a first surface including a first opening and configured to emit the light toward a target object through the first opening; and
        a second surface including a second opening and configured to emit the light toward a living body through the second opening;
    a first light reception unit configured to receive first light from the target object through the first opening of the first surface;
    a second light reception unit configured to receive second light from the living body through the second opening of the second surface; and
    a deflection unit configured to deflect one part of the light and transmit another part of the light, wherein
    the deflection unit deflects the one part of the light emitted from the light source unit toward the first opening of the first surface, and transmits the another part of the light emitted from the light source unit toward the second opening of the second surface,
    the light emitted from the light source unit includes light having a first wavelength and light having a second wavelength different from the first wavelength,
    the deflection unit deflects the light having the second wavelength toward the target object and deflects the light having the first wavelength toward the living body,
    the light emitted from the light source unit includes light having a third wavelength longer than the first wavelength,
    the deflection unit deflects the light having the third wavelength toward the living body, and
    the second light reception unit includes a first light reception member configured to receive the light having the first wavelength and a second light reception member configured to receive the light having the third wavelength.

2. The input device according to claim 1, wherein
    the first surface is a surface of the case configured to come into contact with the target object and not configured to come into contact with the living body and
    the second surface is a surface of the case configured to come into contact with the living body and not configured to come into contact with the target object.

3. The input device according to claim 1, wherein
    the case includes:
        a lower case unit including the first surface; and
        an upper case unit covering the first surface and including the second surface, and
    the upper case unit includes the second surface at one end side of the case in a short direction.

4. The input device according to claim 1, wherein
    the case includes:
        a lower case unit including the first surface; and
        an upper case unit covering the first surface and including the second surface, and
    the upper case unit includes:
        a movable portion being movable at one end side of the case in a longitudinal direction; and
        the second surface at the other end side of the case in the longitudinal direction.

5. The input device according to claim 1, further comprising:
    an optical member between the light source unit and the deflection unit.

6. The input device according to claim 5, wherein
    the optical member is a condensing lens.

7. The input device according to claim 1, wherein
    the second wavelength is shorter than the first wavelength.

8. The input device according to claim 1, wherein
    the first light reception member includes a first color filter configured to transmit the light having the first wavelength and configured to block the light having the second wavelength and the light having the third wavelength, and
    the second light reception member includes a second color filter configured to transmit the light having the third wavelength and configured to block the light having the first wavelength and the light having the second wavelength.

9. A biometric information detection device, comprising:
    the input device according to claim 1; and
    the information processing device configured to communicate with the input device, wherein
    the input device is movably provided and
    a control unit is provided, the control unit being configured to detect a moving direction of the input device, based on reception of the first light at the first light reception unit, and detect biometric information about a user, based on reception of the second light at the second light reception unit.

10. The biometric information detection device according to claim 9, wherein
    when the second light reception unit receives the second light, the control unit detects the moving direction of the input device, based on the reception of the second light at the second light reception unit.

11. The biometric information detection device according to claim 9, wherein
    the control unit transmits information relating to the biometric information about the user to the information processing device.

12. The biometric information detection device according to claim 9, further comprising:
    a detection member configured to detect movement of the input device, wherein
    when the detection member detects the movement of the input device, the control unit detects the biometric information about the user, based on the reception of the second light at the second light reception unit.

* * * * *